US00PP18507P3

(12) United States Plant Patent
Cockcroft et al.

(10) Patent No.: US PP18,507 P3
(45) Date of Patent: Feb. 19, 2008

(54) SHRUB ROSE PLANT NAMED 'RADTKOPINK'

(50) Latin Name: *Rosa hybrida*
Varietal Denomination: cv. Radtkopink

(75) Inventors: David F. Cockcroft, Simsbury, CT (US); Jerome A. Lavallee, Agawam, MA (US); Jason N. Brown, Elkton, MD (US)

(73) Assignee: CP Delaware, Inc., Wilmington, DE (US)

( * ) Notice: Subject to any disclaimer, the term of this patent is extended or adjusted under 35 U.S.C. 154(b) by 10 days.

(21) Appl. No.: 11/471,610

(22) Filed: Jun. 21, 2006

(65) Prior Publication Data

US 2007/0300332 P1 Dec. 27, 2007

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of Landscape Shrub Rose Plant is provided that abundantly and substantially continuously forms attractive bright pink double blossoms. Such blossom coloration can be distinguished from the bright red coloration of the parential 'Radtko' variety (U.S. Plant Pat. No. 16,202). A round and bushy growth habit is displayed. The ornamental green foliage displays a satiny finish and contrasts nicely with the blossom coloration. Excellent resistance to blackspot as well as very good winter hardiness have been observed.

3 Drawing Sheets

Botanical/commercial classification: *Rosa hybrida*/Shrub Rose Plant.
Varietal denomination: cv. Radtkopink.

SUMMARY OF THE INVENTION

A single plant of the new variety was discovered at Granby, Conn., U.S.A. while growing among a group of 500 plants of the 'Radtko' variety (U.S. Plant Pat. No. 16,202). The plant was approximately three years of age and have been asexually reproduced by the rooting of a cutting of the 'Radtko' variety. The plant displayed a distinctive bright pink blossom coloration unlike that of its parent, and is considered to be a whole plant mutation of the 'Radtko' variety that is of unknown causation. The plant subsequently has undergone detailed observation and study at West Grove, Pa., U.S.A., and it has been determined that it constitutes a new variety that can be distinguished from its parental variety as well as all other landscape shrub rose varieties known to Applicants.

It was found that the new variety of landscape shrub rose plant of the present invention possesses the following combination of characteristics:

(a) abundantly and substantially continuously forms attractive double blossoms that are bright pink in coloration unlike the red blossoms of the 'Radtko' variety (U.S. Plant Pat. No. 16,202), (b) exhibits a round and bushy growth habit, (c) forms vigorous vegetation, (d) forms attractive ornamental green foliage with a satiny finish, and (e) exhibits excellent resistance to blackspot.

The blooming cycle is believed to be one of the longest observed to date and is generally comparable to that of the 'Radtko' and 'Radrazz' (U.S. Plant Pat. No. 11,836) varieties. Also, the winter hardiness has been very good during observations to date.

The new variety well meets the needs of the horticultural industry. It can be grown to advantage as attractive ornamentation in parks, gardens, public areas, and in residential settings. It is particularly well suited for growing in the landscape. The bright pink blossoms contrast nicely with the satiny green foliage.

The new variety of the present invention can be readily distinguished from its parental 'Radtko' variety in view of its distinctive blossom color. More specifically, the new variety forms bright pink double blossoms while the double blossoms of the 'Radtko' variety are bright red. Additionally, the new variety can be readily distinguished from the 'Radrazz' variety (U.S. Plant Pat. No. 11,836), the 'Radyod' variety (U.S. Plant Pat. No. 14,700), the 'Radcon' variety (U.S. Plant Pat. No. 15,070), and the 'Radcor' variety (U.S. Plant Pat. No. 17,346). The blossoms of each of these varieties are single, while the blossoms of the new variety are double. Also, the blossoms of the 'Radrazz' variety are bright red, the blossoms of the 'Radyod' variety light pink, the blossoms of the 'Radcon' variety are slightly darker pink than those of the 'Radyod' variety, and the blossoms of the 'Radcor' variety are light coral pink with a yellow eye.

The characteristics of the new variety have been found at West Grove, Pa., U.S.A. and at Waso, Calif. U.S.A., to be homogeneous and stable and are strictly transmissible by asexual propagation such as budding, grafting, and the rooting of cuttings from one generation to another. The new variety reproduces true to type by such asexual propagation.

The new variety has been named the 'Radtkopink,' and will be marketed under the PINK DOUBLE KNOCK OUT trademark.

BRIEF DESCRIPTION OF THE PHOTOGRAPHS

The accompanying photographs show, as nearly true as it is reasonably possible to make the same in color illustrations of this character, typical specimens of the new variety. The rose plants of the new variety illustrated herein were approximately three years of age and were observed during May, 2006, while growing outdoors on their own roots near West Grove, Pa., U.S.A.

DETAILED DESCRIPTION

Figure 1:
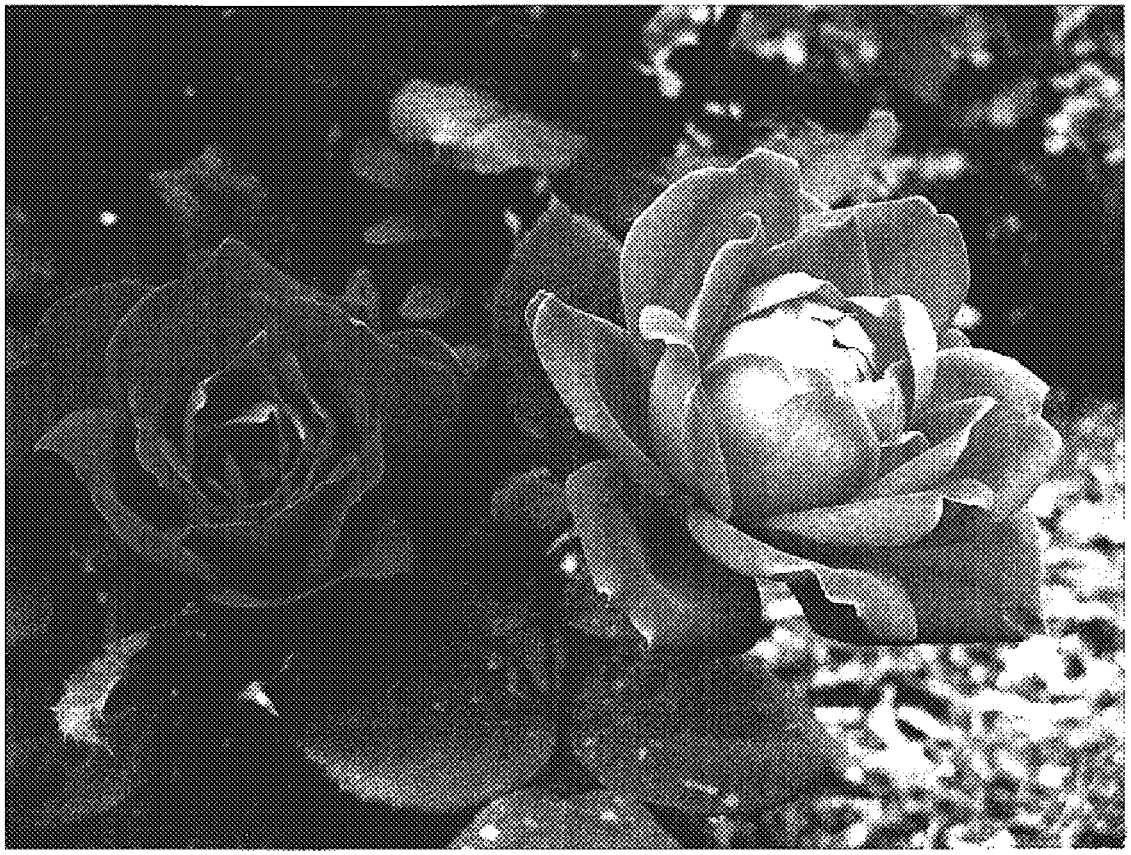
FIG. 1 illustrates for comparative purposes typical double blossoms of the 'Radtko' parent variety (left) and the new 'Radtkopink' variety (right). The bright red blossom coloration of the parent is shown as is the bright pink coloration of the new 'Radtkopink' variety.
Figure 2:
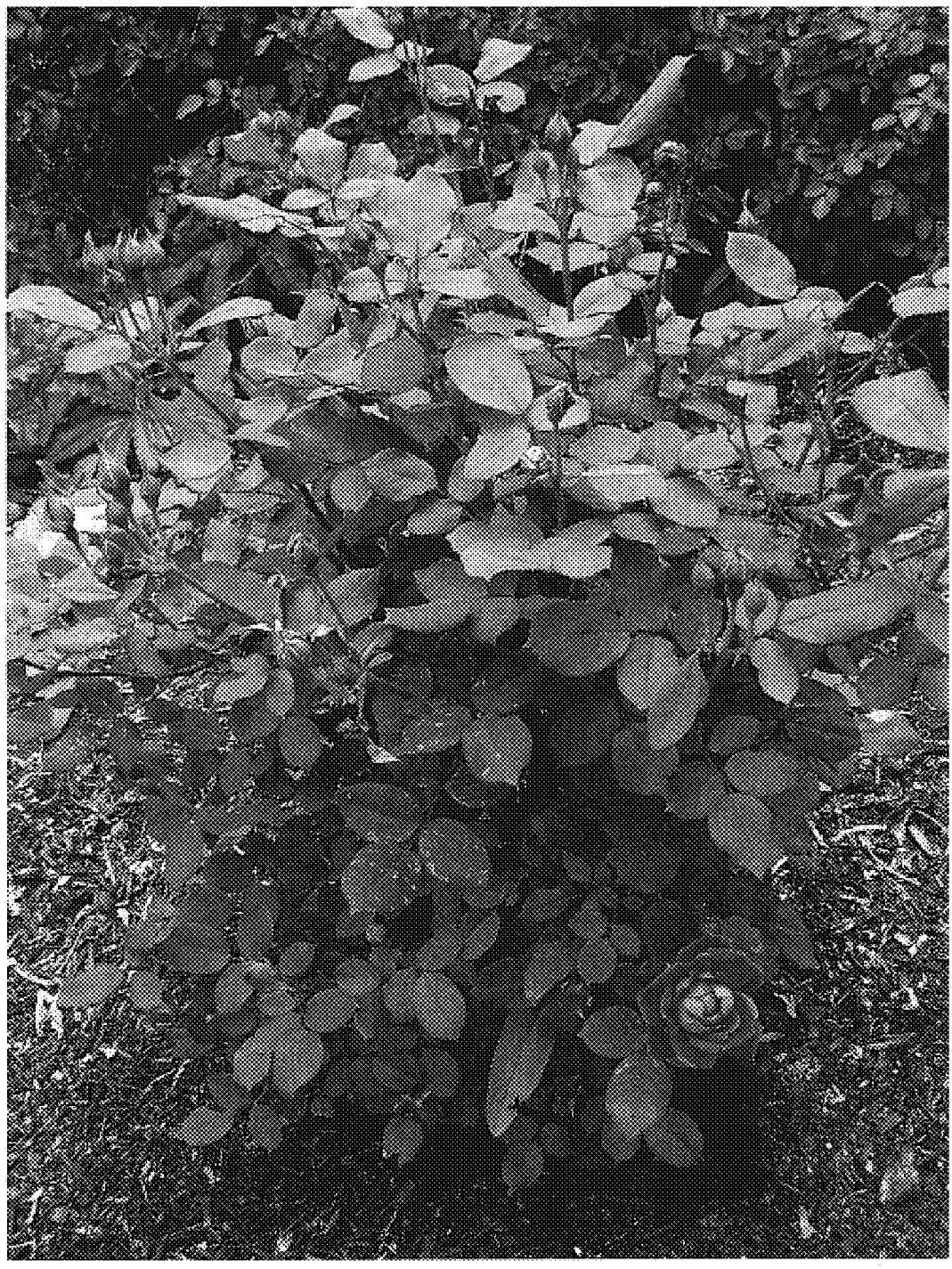
FIG. 2 illustrates the typical round and bushy growth habit of the new 'Radtkopink' variety when beginning to flower.
Figure 3:
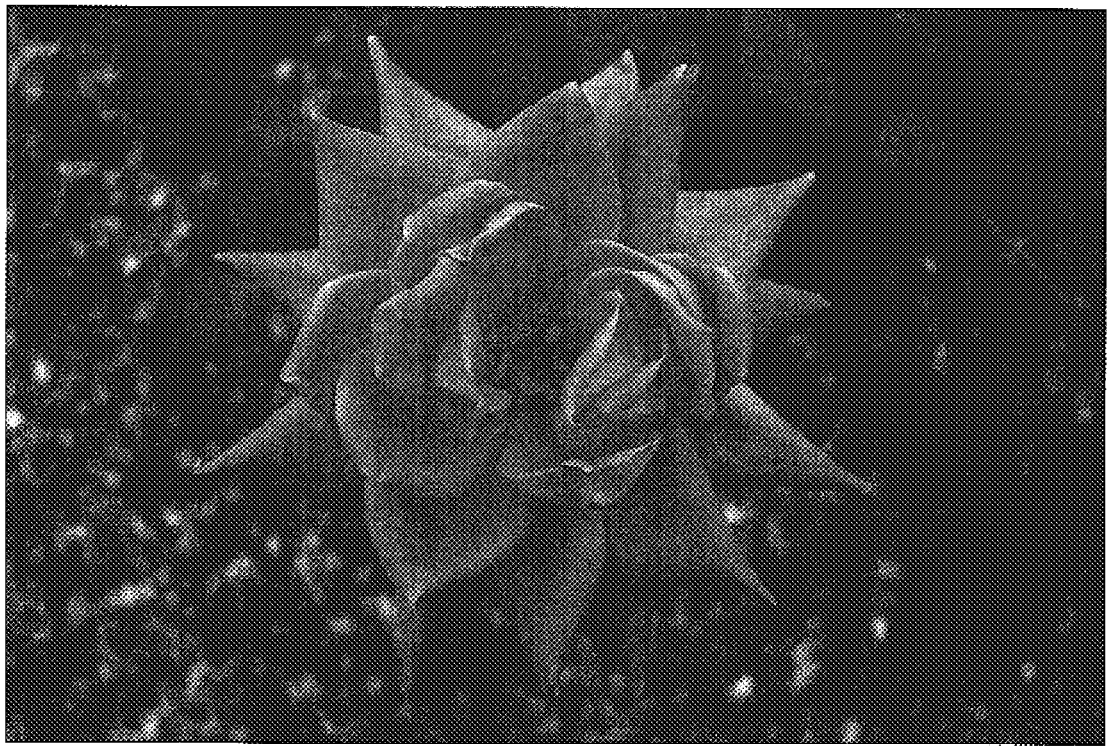
FIG. 3 illustrates a typical fully open double bright pink blossom of the new 'Radtkopink' variety in its final stage wherein the reproductive organs are exposed.

The chart used in the identification of colors is that of The Royal Horticultural Society (R.H.S. Colour Chart), London, England. The description is based on the observation of two year-old specimens of the new variety during October while growing outdoors on their own roots near West Grove, Pa., U.S.A.

Class: Landscape Shrub Rose.

Plant:

*Height.*—Approximately one meter on average at the end of the growing season.

*Width.*—Approximately one meter on average at the end of the growing season.

*Habit.*—Round, and bushy.

Branches:

*Color.*—Young stems: near Yellow-Green Group 144B with some highlights of Red Group 53A. Adult wood: Yellow-Green Group 144B suffused with Greyed-Purple Group 184A.

*Texture.*—Stems bear a smooth surface texture when young and when mature.

*Thorns.*—Size: approximately 1 to 1.5 cm in length on average with some smaller bristles/prickles near the peduncle. Color: near Greyed-Green Group 195A when immature, and near Greyed-Purple Group 184B when mature.

Leaves:

*Stipules.*—Parallel with the auricle facing outward, approximately 8 mm in length, approximately 4 mm in width, and near Greyed-Green Group 191B in coloration.

*Auricle.*—Approximately 8 mm in size, and Yellow-Green Group 146C in coloration.

*Petioles.*—Upper surface: Yellow-Green Group 144B, and commonly approximately 2 cm in length. Under surface: Yellow-Green Group 144B with highlights of Greyed-Purple Group 184A and some prickles.

*Size.*—A five-leaflet leaf commonly is approximately 9.1 cm in length on average and approximately 7 cm in width on average.

*Leaflets.*—Number: 3, 5, and 7. Shape: Ovate with a serrulate margin, rounded base, and an acuminate tip. Margins: serrulate. Texture: smooth on both surfaces. Leaflet size: commonly approximately 7 cm in length on average for a terminal leaflet. Overall appearance: very dense, leathery, and medium green in coloration, with a satiny finish. Color (young foliage): Upper surface: Greyed-Purple Group 187A with highlights of Green Group 141D. Under surface: Greyed-Purple Group 187B. Color (adult foliage): Upper surface: commonly between Yellow-Green Group 147A and Green Group 136A. Under surface: Yellow-Green Group 147B with some Yellow-Green Group 148D.

Inflorescence:

*Number of flowers.*—Commonly approximately 4 blooms on average in a cluster.

*Peduncle.*—Moderately strong, medium green, Green Group 141D, with some small prickles, approximately 4 cm in length on average.

*Sepals.*—Upper surface: between Yellow-Green Group 144B with areas of White Group 144B and some pubescence. Under surface: Yellow-Green Group 144A and 144B. Number: five. Size: commonly approximately 22 mm in length on average, and approximately 8 mm in width on average at the widest point. Apex: acuminate. Extensions: subulatus with a serrulate margin.

*Buds.*—Shape: slender. Length: approximately 2.5 cm on average. Width: approximately 1.75 cm on average. Size: small to medium. Color (when opening): upper surface: commonly between Red-Purple Group 60B and 60C. Under surface: commonly between Red-Purple Group 60B and 60C.

*Flower.*—Form: double and informal. Diameter: approximately 7 to 8 cm. on average. Color (when opening begins): Upper surface: commonly between Red-Purple Group 66A and 66B with a small amount of Yellow-Green Group 154B at the base of the petals. Under surface: commonly between Red-Purple Group 62B and 62C with a small amount of Yellow-Green Group 154B at the base of the petals. Color (when blooming): Upper surface: commonly between Red-Purple Group 61C and 61D, and Red Group 54A at the base. Under surface: commonly between Red-Purple Group 62A, lighter at the center, and Red Group 50C at the base. Color (at end of blooming): Upper surface: commonly between Red-Purple Group 64C and 64D, and lighter at the center. Under surface: commonly between Red-Purple Group 62C and 62D. Fragrance: mild spice. Petal form: Wedge-shaped with a curled apex. Petal number: Approximately 30 to 35 on average. Petaloids: none observed. Lasting quality: blossoms commonly last approximately two weeks on the plant and approximately two weeks when cut and placed in a vase. Petal drop: very good, the petals drop cleanly and freely. Stamen number: approximately 65 on average. Anthers: approximately 3 mm in length on average, approximately 1.8 mm in width on average, and Greyed-Yellow Group 162B in coloration. Filaments: commonly approximately 3 mm in length, and Red Group 48D in coloration. Pistils: are separate and free, and number approximately 27 on average. Stigmas: Yellow Group 13C in coloration. Styles: commonly approximately 3 mm in length, and Red Group 45B in coloration. Receptacle: smooth, with achenes standing on the bottom and wall, commonly measures approximately 5 mm×7 mm, and Green Group 141C in coloration.

Development:

*Vegetation.*—Vigorous and strong.

*Blossoming.*—Abundant and substantially continuous.

*Hardiness.*—Very good, and has withstood −20° F.

*Resistance to diseases.*—Excellent with respect to blackspot and rust.

*Formation of hips/seeds.*—Sparse.

We claim:

1. A new and distinct landscape shrub rose plant characterized by the following combination of characteristics:

(a) abundantly and substantially continuously forms attractive double blossoms that are bright pink in coloration unlike the red blossoms of the 'Radtko' variety (U.S. Plant Pat. No. 16,202), (b) exhibits a round and bushy growth habit, (c) forms vigorous vegetation, (d) forms attractive ornamental green foliage with a satiny finish, and (e) exhibits excellent resistance to blackspot;

substantially as herein shown and described.

* * * * *